United States Patent
McCormick

(10) Patent No.: US 6,362,339 B1
(45) Date of Patent: Mar. 26, 2002

(54) METHOD OF MAKING METAL 8-QUINOLINOLATO COMPLEXES

(75) Inventor: Fred Boyle McCormick, Maplewood, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/413,415

(22) Filed: Oct. 6, 1999

(51) Int. Cl.⁷ .................... C07D 215/20; C07D 215/36
(52) U.S. Cl. .......................... 546/7; 546/179
(58) Field of Search .................... 546/7, 179

(56) References Cited

U.S. PATENT DOCUMENTS

| | | |
|---|---|---|
| 3,300,498 A | 1/1967 | Gershon et al. |
| 4,720,432 A | 1/1988 | Van Slyke et al. ........... 428/457 |
| 5,061,569 A | 10/1991 | Van Slyke et al. ........... 428/457 |
| 5,141,671 A | 8/1992 | Bryan et al. ........... 252/301.16 |

FOREIGN PATENT DOCUMENTS

| | | |
|---|---|---|
| EP | 0 525 904 A | 2/1993 |
| JP | 63-128041 | 5/1988 |
| JP | 5279371 | 10/1993 |
| JP | 07 196620 A | 8/1995 |

OTHER PUBLICATIONS

Sapochak, Chemical Abstracts 126:12568, 1996.*
Hiratani, Chemical Abstracts 125:167808, 1995.*
Kato, Chemical Abstracts 109:232151, 1988.*
"Chemical Abstracts", vol. 120, No. 20, May 16, 1994, Columbus, OH, Abstract No. 259967.
"Chemical Abstracts", vol. 74, No. 6, Feb. 8, 1971, Columbus, OH, Abstract No. 27607t.
C.H. Chen, J. Shi, and C.W. Tang "Recent Developments in Molecular Organic Electroluminescent Materials", *Macromolecular Symposia*, 1997, 125, pp. 1–48.
J. Kido, "Organic Electroluminescent Devices Based on Polymeric Materials", *Trends in Polymer Science*, Oct. 1994, vol. 2, No. 10, pp. 350–355.
Wagner et al., "Purification and Characterization of Phthalocyanines", *Journal of Material Science.*, 17, 1982, pp. 2781–2791.

* cited by examiner

*Primary Examiner*—D. Margaret Seaman
(74) *Attorney, Agent, or Firm*—Melanie Gover

(57) ABSTRACT

A method for making metal (8-quinolinolate) complexes from air and moisture stable reagents is described. For example, the making of aluminum tris(quinolinolates), such as tris(8-hydroxyquinolinato), from aluminum (III) carboxylates, such as aluminum lactate and aluminum stearate, is described. Examples of bis and tris metal (8-quinolinolates) as well as single and mixed ligand complexes are given.

13 Claims, No Drawings

METHOD OF MAKING METAL 8-QUINOLINOLATO COMPLEXES

TECHNICAL FIELD

This invention relates to a method of making metal 8-quinolinolato complexes.

BACKGROUND

Aluminum tris(8-quinolinolates), particularly tris(8-hydroxyquinolinato) aluminum (AlQ), have become standard emitter and electron transport materials for small molecule organic light emitting diodes (OLEDs) such as those described in U.S. Pat. No. 5,061,569 and C. H. Chen, J. Shi, and C. W. Tang, "Recent Developments in Molecular Organic Electroluminescent Materials," *Macromolecular Symposia*, 1997, 125, 1–48. Other metal 8-quinolinolato complexes have also been shown to be useful electron transport materials for OLEDs. Reported methods for making these compounds have required moisture sensitive reagents such as metal alkoxides and metal halides, which may require special handling procedures. In addition, these methods may not provide products of sufficient purity for the fabrication of OLEDs without the need for special purification techniques such as train sublimation (Wagner et al., *J. Mat. Sci.*, 17, 2781 (1982)). Such purifications are difficult to perform on a large scale and pose a significant barrier to the large scale manufacturing of OLEDs.

SUMMARY OF INVENTION

Because of the high potential demand for AlQ, a simple method for large-scale, high purity synthesis of this compound, and related metal 8-quinolinolato complexes, without the use of air- and moisture-sensitive reagents, would be desirable. Disclosed herein are novel methods for making metal 8-quinolinolato complexes using easily-handled, inexpensive, and commercially available metal carboxylates such as aluminum lactate, aluminum stearate, and zinc acetate.

One aspect of the invention features the preparation of metal 8-quinolinolato complexes by the reaction of metal carboxylates with 8-hydroxyquinoline compounds represented by Formula I:

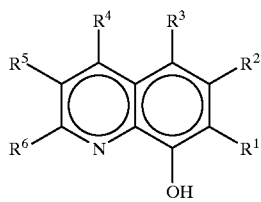

where $R^6$=hydrogen and $R1$–$R^5$=hydrogen, halogen, cyano, alkyl, aryl, alkoxy, aryloxy, part of a fused aromatic or aliphatic ring system, and each $R1$–$R^5$ group may incorporate further substituents.

Another aspect of the invention features bis and tris metal (8-quinolinolate) complexes.

Another aspect of the invention features a method of making aluminum tris(8-quinolinolates) comprising combining an aluminum (III) carboxylate material with at least three equivalents of an 8-hydroxyquinoline compound represented by Formula I in an appropriate organic solvent. The carboxylate may be, for example, aluminum stearate or aluminum lactate and the organic solvent may be, for example, ethanol or toluene.

Another aspect of the invention features the production of mixed-ligand metal 8-quinolinolato complexes from the reaction of metal carboxylates with a mixture of different 8-hydroxyquinoline compounds represented by Formula I, including mixed-ligand aluminum 8-quinolinolato complexes from the reaction of aluminum carboxylates and 8-hydroxyquinoline compounds represented by Formula I.

Another aspect of the invention features reaction compositions comprising metal carboxylate material and an 8-hydroxyquinoline represented by Formula I in an organic solvent.

An advantage of at least one embodiment of the present invention is that due to the air and moisture stability of the starting materials used for the synthesis of metal (8-quinolinolates) no inert atmosphere or specially dried solvents are required.

An advantage of at least one embodiment of the present invention is that the reagents are inexpensive and commercially available.

An advantage of at least one embodiment of the present invention is that the reactions described herein can be carried out in essentially any apparatus compatible with hot organic solvents.

An advantage of at least one embodiment of the present invention is that the synthesis reaction is rapid.

An advantage of at least one embodiment of the present invention is that if long reaction times can be tolerated, it may not be necessary to heat the reactions so long as the reactants have sufficient solubility in the chosen solvent.

An advantage of at least one embodiment of the present invention is that high yields of a clean product is obtained in the absence of difficult and lengthy separation and purification processes such as sublimation. The purity of the product allows its immediate incorporation in articles such as organic light emitting diodes.

An advantage of at least one embodiment of the present invention is that the reaction method of the present invention is applicable to the preparation of many metal 8-quinolinolato derivative including those containing a mixture of 8-quinolinolato ligands.

Other features and advantages of the invention will be apparent from the following detailed description, and claims.

DETAILED DESCRIPTION

The present invention describes how metal quinolinato complexes may be made from metal carboxylates and certain 8-hydroxyquinoline compounds having the structure of Formula I:

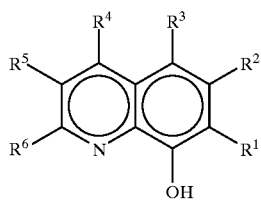

where $R^6$=hydrogen and $R1$–$R^5$=hydrogen, halogen, cyano, alkyl, aryl, alkoxy, aryloxy, part of a fused aromatic or aliphatic ring system, and each $R1$–$R^5$ group may incorporate further substituents. It was found that, for the structure of Formula I, an $R^6$ group larger than hydrogen sterically hindered the bonding of the 8-hydroxyquinoline. Examples of ligands represented by Formula I include 5-(diphenylamino)-8-quinolinol, 7,8,9,10-tetrahydro-6-methyl-4-phenanthridinol, 3,5,7-trichloro-8-quinolinol, 3-decyl-8-quinolinol, 5-[(nonyloxy)methyl]-8-quinolinol, 3-allyl-8-hydroxyquinoline, 4-phenanthridinol, benzo[f]quinolin-5-ol, 5-chloro-8-hydroxyquinoline, 5,7-dichloro-8-hydroxyquinoline, 5-methyl-8-hydroxyquinoline, and 4-methyl-8-hydroxyquinoline. 5-hydroxyquinoxaline and its derivatives are also useful in this invention as are 2-(2-hydroxyphenyl)benzoxazole, 2-(2-mercaptophenyl) benzoxazole, 2-(2-hydroxyphenyl)benzothiazole, 2-(2-mercaptophenyl)benzothiazole and 8-quinolinethiol and their derivatives.

The metal 8-quinolinolates made by the present invention may be represented by Formula II:

$$M(L)_x \quad \text{II}$$

where M is the metal, L is the ligand of Formula I, and x is 2 or 3.

Mixed ligand metal 8-quinolinolato complexes may also be made per the present invention. These complexes may be prepared by reacting a metal carboxylate with a mixture of 8-hydroxyquinoline compounds having the structure of Formula I in an appropriate relative ratio. For example, aluminum lactate may be added to a solution containing two equivalents of 8-hydroxyquinoline and one equivalent of 5-chloro-hydroxyquine to produce bis(8-hydroxyquinolinato) aluminum.

Mixed ligand metal 8-quinolinolato complexes are important because they are generally more amorphous than their single ligand counterparts. Thus, vapor deposited small molecule OLEDs will be more stable and have a longer lifetime since the amorphous glass electron transport layers formed by the mixed ligand metal quinolinato complex will not crystallize as readily as their single ligand counterparts during OLED storage or operation. The mixed ligand quinolinato complexes will also have greater solubility in organic solvents making them more useful than their single ligand counterparts in solution-cast molecularly doped polymer OLEDs such as those described in J. Kido, "Organic Electroluminescent Devices Based on Polymeric Materials," Trends in Polymer Science, 1994, 2, 350–355.

An example of a reaction of the present invention is the preparation of AlQ by the reaction of aluminum (III) carboxylates, such as commercially available and inexpensive aluminum stearate ($[CH_3(CH_2)_{16}CO_2]_3Al$, $C_{54}H_{105}AlO_6$) and aluminum lactate ($[CH_3CH(OH)CO_2]_3Al$, $C_9H_{15}AlO_9$), with at least three equivalents of 8-hydroxyquinoline ($C_9H_7NO$) in a compatible organic solvent to give aluminum tris(8-quinolinolato) ($C_{27}H_{18}AlN_3O_3$) (AlQ), in nearly quantitative yields This type of reaction is represented by equation 1:

(eq. 1)

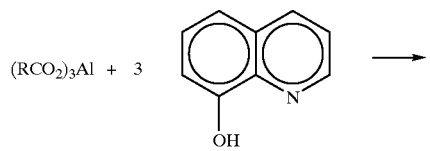

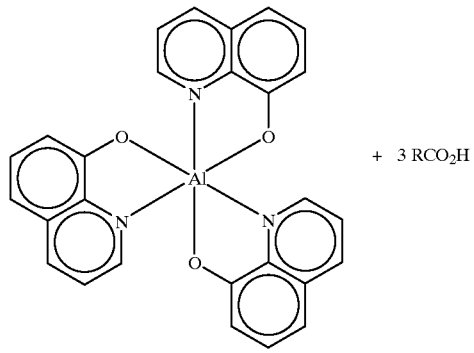
+ 3 RCO$_2$H where R is a branched, straight chain, or cyclic alkyl group having from 1 to 20, preferably 2 to 17 carbon atoms, wherein the alkyl or cycloalkyl groups can have one or more substituents such as hydroxy, ether, and halogen.

An example of a reaction represented by equation 1 is the preparation of AlQ by the reaction of aluminum lactate with 8-hydroxyquinoline in ethanol. In this preparation, both the aluminum lactate and 8-hydroxyquinoline are at least partially soluble in ethanol, while the resulting AlQ is not. A similar reaction of aluminum stearate with 8-hydroxyquinoline in ethanol also gave high yields of AlQ, but the product was less pure.

Toluene proved to be a more suitable solvent for the reaction of aluminum stearate with 8-hydroxyquinoline because both starting materials and stearic acid are readily soluble in toluene while the AlQ product is only sparingly soluble, allowing for easy separation of the AlQ. The reaction was rapid, with fine, needle-like crystals of AlQ appearing in the reaction vessel as the reaction mixture was warmed. High yields were obtained.

Reaction of aluminum stearate with 8-hydroxyquinoline in refluxing heptane precipitated AlQ during the course of the reaction. However, the inventors have found that this precipitate also contained significant amounts of stearic acid byproduct.

One of skill in the art will recognize that some solvents are preferred for a given reaction and that using other solvents may provide poor results. For example, it was found that using toluene as a solvent for aluminum lactate resulted in a low yield due to the low solubility of aluminum lactate in toluene.

Aluminum lactate may generally be a preferred reactant over aluminum stearate. Both aluminum lactate and the lactic acid byproduct are very soluble in water, which simplifies their removal from any crude AlQ products. The lower molecular weight of aluminum lactate also allows the use of a smaller mass, compared to aluminum stearate, of starting material,which can afford a significant advantage in scaling-up and commercial production of AlQ.

The AlQ obtained as a precipitate from the reaction of 8-hydroxyquinoline with aluminum stearate in toluene appears, after collection by filtration, solvent washing, and drying, to be suitable for use in the fabrication of organic electroluminescent (OEL) films, such as those described in U.S. Pat. No. 4,720,432. If desired, AlQ can be further purified by common methods such as recrystallization, sublimation, or Soxhlet extraction.

A lamp using recrystallized AlQ prepared from aluminum lactate in ethanol was fabricated on a glass substrate using vapor deposition techniques. At 20 mA/cm$^2$ the lamp operated at 7.8 V with a luminance of 686 cd/m$^2$. This corresponded to an external quantum efficiency of 1.06%. These values were essentially the same as values obtained from a lamp made using commercially available sublimed AlQ. Thus, the method of the invention for the synthesis of aluminum tris(8-quinololates) can provide large quantities of AlQ suitable for the production of OEL films.

In addition to the aforementioned aluminum stearate and lactate, a variety of aluminum tris(carboxylates) may be useful for the present invention including aluminum octoate, aluminum palmitate, and aluminum oxalate. Basic aluminum carboxylates of the general structure $(RCO_2)_2AlOH$, such as boric acid stabilized aluminum acetate, may also be useful in this invention, where R is the same as described in equation 1.

Other metal 8-quinolinolato complexes can be prepared by the method of this invention. Examples of metal carboxylates that may be useful as starting materials include barium acetate, cadmium acetate, dyspropium acetate, indium acetate, neodinium(2-ethylhexanoate), samarium naphthanate, and zinc acetate.

The invention may be illustrated by way of the following examples.

EXAMPLES

Unless otherwise specified, all materials were obtained from, or are available from, Aldrich Chemical Co., Milwaukee, Wis.

Test Methods

Glass substrates coated with indium-tin oxide (ITO) have nominal sheet resistance of 10–100 ohm/square and ITO thickness of 300–1500 Å.

Vacuum deposition was carried out in an evaporator vacuum chamber equipped with an oil diffusion pump to operate at a base pressure of $10^{-6}$ tor and six evaporant sources that were heated by resistive heating. Deposition rates were monitored using an oscillating-crystal thickness monitor (Inficon XTC/2, Leybold Inficon, East Syracuse, N.Y.). The substrate was nominally kept at 23° C.

Light output intensity was obtained using a United Photodetectors model #PIN-10D silicon photodetector (UDT Sensors, Hawthorne, Calif.).

Electroluminescence emission spectra were obtained using a calibrated SD1000 fiber optic spectrometer (Ocean Optics, Inc., Dunedin, Fla.).

Example 1

Preparation of AlQ from Aluminum Lactate and 8-hydroxyguinoline in Ethanol.

Aluminum lactate, $Al[CH_3CH(OH)CO_2]_3$, (10.0 g) and 8-hydroxyquinoline (16.0 g) were placed in a 250 mL round bottomed flask equipped with a magnetic stir bar and a reflux condenser. Ethanol (150 mL, denatured) was added and the cream colored slurry was stirred magnetically. The flask was heated to reflux by means of an electric heating mantle and reflux was maintained for 17 hours. Upon initial heating, the cream colored slurry gradually became yellowish in color. The yellow color intensified as the reaction progressed and the reaction mixture remained heterogeneous throughout the reflux period. After cooling, the reaction mixture was filtered and the yellow filter cake was sequentially washed with two 50 mL portions of ethanol, two 50 ml portions of distilled water, two 50 mL portions of ethanol, and two 50 mL portions of diethyl ether. The filter cake was air dried for 24 hours to give 14.9 g of tris(8-quinolinolato)aluminum as a bright yellow powder. The $^1$H-NMR spectrum of the powder matched that of a commercial sample of tris(8-quinolinolato)aluminum. The powder was dissolved in hot $CHCl_3$ and filtered through a medium porosity glass frit. Addition of heptane and cooling to approximately 0° C. caused fine yellow needles of AlQ to precipitate from the yellow filtrate. the needles were collected by filtration, washed with petroleum ether, vacuum dried, and used to fabricate an electroluminescent lamp.

Example 2

Preparation of AlQ from Aluminum Stearate and 8-hydroxyquinolinc in Toluene.

Aluminum stearate, $Al[CH_3(CH_2)_{16}CO_2]_3$, (10.0 g, Fisher Scientific Co., Pittsburgh, Pa., technical grade) was placed in a 250 mL round bottomed flask equipped with a magnetic stir bar and a reflux condenser. Toluene (50 mL) was added to give a white slurry. Separately, a 6.0 g sample of 8-hydroxyquinoline (41.3 mmol) was dissolved in 150 mL of toluene and the solution was gravity filtered through a coarse glass frit into the reaction flask. This removed an insoluble minor impurity found in the 8-hydroxyquinoline. After the addition of the 8-hydroxyquinoline to the aluminum stearate-toluene solution, the reaction flask was heated to reflux by means of an electric heating mantle. As the reaction warmed, but prior to refluxing, a large quantity of a fine yellow solid precipitated. The reaction mixture was refluxed for approximately 72 hours, cooled, and filtered. The yellow filter cake was washed sequentially with two 50 mL portions of toluene and two 50 mL portions of petroleum ether. After vacuum drying, the filter cake provided 5.4 g of tris(8-quinolinolato)aluminum as fine yellow needles. An $^1$H-NMR of the product precipitated from the toluene reaction mixture showed no significant resonances other than those of the desired product.

Example 3

Fabrication and Characterization of Electroluminescent Films Using, AlQ of the Invention.

Glass substrates with indium-tin oxide (ITO) coatings were purchased from Thin Film Devices, Inc., Anaheim, Calif. Typical ITO sheet resistance was 10–100 ohm /sq. The ITO/glass was rinsed with methanol and dried with $N_2$. It was then placed in a spinner, covered with xylune, and spun dry. Polyaniline (PANI) (experimental. externally doped material obtained from Monsanto Co., St. Louis, Mo.) dissolved in xylene (typically, 5% solids by weight) was applied through a 0.2 $\mu$m filter to cover the substrate. The substrate was spun at 5000 rpm for 20 seconds, providing a polyani line film of about 1500 Å thickness. The substrate was then immediately moved to an evaporator vacuum chamber and the chamber was evacuated to roughly $10^{-6}$ torr. The evaporator included sources for CuPc, AlQ, TPD, LiF, Al and Sn. All sources were resistively heated tungsten boats. The standard OEL construction was vapor deposited on the PANI- and ITO-coated glass substrate in this order: 50 Å copper phthalocyanine (CuPc), 200 ÅN,N'-bis(3-methylphenyl)-N,N'-diphenylbenzidine (TPD), 350 ÅAlQ, 10 ÅLiF, 2.0 micrometers ($\mu$m) Al, and 1.6 $\mu$m Sn. Deposition rates were typically 2 Å/s for CuPc, AlQ and TPD, 1 Å/s for LiF, and 50–70 Å/s for Al and Sn. Lamps were made with this process, using recrystallized AlQ as prepared in Example 1. These devices operated at 7.8 V and 20 mA/cm$^2$ while emitting 686 cd/m$^2$ of light. The emission spectrum was typical of AlQ. These values were typical of those achieved in lamps using commercially available AlQ.

COMPARATIVE Example 4

Fabrication and Characterization of Electroluminescent Films Using Commercial AlQ.

An ITO-coated glass substrate, 5 cm×7.6 cm×1 mm (Thin Film Devices, Inc., Anaheim, Calif.) was rinsed with methanol and dried under a nitrogen flow, then placed in a spin-coater, covered with xylene, then spun dry. A xylene solution of sulfonic-acid doped PANI (5% solids by weight, non-commercial sample supplied by Monsanto Co., St. Louis, Mo.) was applied through a 0.2 µm TEFLON filter (Gelman Sciences, Ann Arbor, Mich.) to cover the slide. The slide was spun at 5000 rpm for 20 seconds to give a PANI film approximately 1500 Å thick. The coated slide was immediately placed in an evaporator vacuum chamber and the chamber was sealed and evacuated to approximately $10^{-6}$ torr. A light-emitting construction was prepared on the PANI surface by vacuum deposition, in the following order, of: 130 Å CuPc (at 2 Å/sec); 200 Å TPD (at 2 Å/sec); 350 Å AlQ (sublimed grade, Dojindo Laboratories, Kumamoto, Japan) (at 2 Å/sec); 10 Å lithium fluoride (at 1 Å/sec); 5800 Å aluminum (at 60 Å/sec)and 2200 Å indium (at 70 Å/sec). The device operated at 6.06 V and 20 mA/cm² while emitting 540 cd/m² of light.

COMPARATIVE Example 5

Attempted Preparation of bis(2-methyl-8-quinolinolato) (phenolate)aluminum from Pluminum Lactate, 2-methyl-8-hydroxyQuinoline, and Phenol in Methanol.

A solution of 2-methyl-8-hydroxyquinoline (2.0 g) and phenol (1.0 g) in methanol (50 mL) was heated to reflux. Aluminum lactate (1.2 g) was added to the solution. The solution became yellow in color and homogeneous after several minutes. The solution showed a very faint yellow luminescence when illuminated with a blacklight (365 nm). After two hours of heating, the solution remained homogeneous and yellow in color. The solution was stirred while being heated to reflux for a total of 16 hours. The solution remained homogenous and yellow in color during the entire heating time. After standing for an additional 6 days, the solution remained unchanged and no precipitate formed.

COMPARATIVE Example 6

Preparation of bis(2-methyl-8-quinolinolato)(phenolate) aluminum from Aluminum Isopropoxide, 2-methyl-8-hydroxyquinoline and Phenol in Methanol.

A solution of 2-methyl-8-hydroxyquinoline (2.0 g) and phenol (1.0 g) in methanol (50 mL) was heated to reflux. Aluminum isopropoxide (0.8 g) was added to the solution. The solution became yellow in color and homogeneous after several minutes. The solution showed a bright greenish-blue luminescence when irradiated with a blacklight (365 nm). After two hours of heating, a large amount of a pale colored precipitate had formed. The pale precipitate showed a bright blue-white luminescence when irradiated with a blacklight. The solution was stirred while being heated to reflux for a total of 16 hours. The precipitate was collected by filtration, and washed with methanol and petroleum ether. After air drying, 1.58 g of bis(2-methyl-8-quinolinolato)(phenolate) aluminum was obtained as an off-white solid. This product was identical to an authentic sample prepared by the method disclosed in U.S. Pat. No. 5,141,671.

Comparative examples 5 and 6 show that the reactivity of aluminum carboxylates does not mimic the reactivity of aluminum alkoxides and that sterically hindered 8-hydroxyquinolines do not react well with aluminum carboxylates.

COMPARATIVE Example 7

Attempted Preparation of bis(2-methyl-8-quinolinolato) (phenolate)aluminum from Aluminum Stearate, 2 -methyl-8-hydroxyquinoline, and Phenol in Toluene.

A solution of 2-methyl-8-hydroxyquinoline (2.0 g) and phenol (1.0 g) in toluene (50 mL) was heated to reflux. Aluminum stearate (3.4 g) was added to the solution. The solution became tannish yellow in color and homogeneous after several minutes. The solution showed a blue-green luminescence when illuminated with a blacklight (365 nm). The solution was stirred and refluxed for 16 hours. Upon cooling to room temperature, the solution remained homogeneous and yellow in color. After standing for an additional 6 days, the solution remained unchanged and no precipitate formed.

COMPARATIVE Example 8

Preparation of bis(2-methyl-8-quinolinolato)(phenolate) aluminum from Aluminum Isopropoxide, 2-methyl-8-hydroxyguinoline, and Phenol in Toluene.

A solution of 2-methyl-8-hydroxyquinoline (2.0 g) and phenol (1.0 g) in toluene (50 mL) was heated to reflux. Aluminum isopropoxide (0.8 g) was added to the solution. The solution became tannish yellow in color and homogeneous after several minutes. The solution showed a bright blue-white luminescence when irradiated with a blacklight (365 nm). The solution was stirred and refluxed for 16 hours. Upon cooling to room temperature, a large amount of a pale colored precipitate had formed. The pale precipitate showed a bright blue-white luminescence when irradiated with a blacklight. The precipitate was collected by filtration and washed with petroleum ether. After air drying, 1.55 g of bis(2-methyl-8-quinolinolato)(phenolate)aluminum was obtained as an off-white crystalline solid. This product was identical to an authentic sample prepared by the method disclosed in U.S. Pat. No. 5,141,671.

Comparative examples 7 and 8 show that the reactivity of aluminum carboxylates does not mimic the reactivity of aluminum alkoxides and that sterically hindered 8-hydroxyquinolines do not react well with aluminum carboxylates.

Example 9

Preparation of tris(5-chloro-8-hydroxyquinolinato) aluminum from 5-chloro-8-hydroxyquinoline and Aluminum Lactate in Ethanol.

Aluminum lactate (5.0 g) and 5-chloro-8-hydroxyquinoline (10.0 g) were placed in a 250 mL Erlenmeyer flask and 200 mL of ethanol was added. The resulting white slurry was heated to reflux on a hot plate and the solids gradually dissolved. After 15 minutes, large amounts of a bright yellow solid began to precipitate. The reaction was stirred at reflux for two hours and then was stirred at room temperature for 15 hours. The reaction mixture was then filtered and the yellow filter cake was sequentially washed with ethanol and petroleum ether. After air drying, 7.4 g of tris(5-chloro-8-hydroxyquinolinato)aluminum was obtained as a bright yellow solid that showed a yellow-green luminescence when irradiated with a blacklight.

Example 10

Preparation of tris(5,7-dichloro-8-hydroxyciquinolinato) aluminum from 5,7-dichloro-8-hydroxyquinoline and Aluminum Lactate in Ethanol.

Aluminum lactate (5.0 g) and 5,7-dichloro-8-hydroxyquinoline (12.0 g) were placed in a 1.5 L Erlenmeyer flask and 800 mL of ethanol was added. The resulting beige slurry was heated to reflux on a hot plate and the color began to change to yellow after about 10 minutes. The mixture was heated and stirred for 8 hours. The yellow color became more prominent and the mixture became thicker as product precipitated as a fine powder. The mixture was cooled and filtered to collect the light yellow precipitate. The precipitate was sequentially washed with water and ethanol.

After air drying, 11.2 g of tris(5,7-dichloro-8-hydroxyquinolinato)aluminum was obtained as a light yellow, chalky solid that showed a yellow luminescence when irradiated with a blacklight.

Example 11
Preparation of tris(5-nitro-8-hydroxyquinolinato)aluminum from 5-nitro-8-hydroxyquinoline and Aluminum Lactate in Methanol.

Aluminum lactate (1.0 g) and 150 mL of methanol were placed in a 250 mL Erlenmeyer flask and the mixture was heated to reflux on a hot plate. Two grams of 5-nitro-8-hydroxyquinoline was then added to the cloudy suspension and the mixture was heated and stirred for 9 hours. A yellow precipitate formed and was collected by filtration after the mixture was cooled to room temperature. The precipitate was washed with methanol. After air drying, 1.98 g of tris(5-nitro-8-hydroxyquinolinato)aluminum was obtained as a yellow solid that showed a yellow luminescence when irradiated with a blacklight.

Example 12
Preparation of tris(5,7-dibromo-8-hydroxvguinolinato) aluminum from 5,7-dibromo-8-hydroxyguinoline and Aluminum Lactate in Methanol.

Aluminum lactate (1.0 g) and 150 mL of methanol were placed in a 250 mL Erlenmeyer flask and the mixture was heated to reflux on a hot plate. A 3.12 g sample of 5,7-dibromo-8-hydroxyquinoline was then added to the cloudy suspension and the mixture was heated and stirred for 7 hours. A yellow precipitate formed and was collected by filtration after the mixture was cooled to room temperature. The precipitate was washed with methanol. After air drying, 3.1 g of tris(5,7-dibromo-8-hydroxyquinolinato)aluminum was obtained as a pale yellow solid that showed a greenish-yellow luminescence when irradiated with a blacklight.

Example 13
Preparation of bis(8-hydroxyquinolinato)(5-chloro-8-hydroxyquinolinato)aluminum from 8-hydroxyquinoline, 5-chloro-8-hydroxyquinoline, and Aluminum Lactate in Methanol.

One gram of 8-hydroxyquinoline and 0.61 g of 5-chloro-8-hydroxyquinoline were placed in a 125 mL Erlenmeyer flask and 75 mL of methanol was added. The solution was heated to reflux to give a homogeneous tan solution. One gram of aluminum lactate was added and a yellowish precipitate formed almost immediately. The solution was stirred and heated for 55 hours and was then allowed to cool. The precipitate was collected by filtration and washed with methanol and petroleum ether. After air drying, 0.73 g of bis(8-hydroxyquinolinato)(5-chloro-8-hydroxyquinolinato) aluminum was obtained as a yellow-green solid.

Example 14
Preparation of bis(8-hydroxyquinolinato)zinc from 8-hydroxyquinoline and Zinc Acetate in Methanol.

Zinc acetate dihydrate (1.0 g) was dissolved in 75 ml. of hot methanol and 1.4 g of 8-hydroxyquinoline was added to the homogeneous solution. A yellow precipitate formed after a few minutes and the solution was stirred at reflux for 3 hours. The solution was allowed to cool and the precipitate was isolated by filtration and washed with methanol and petroleum ether. After air drying, 1.44 g of bis(8-hydroxyquinolinato)zinc was obtained as a bright yellow solid.

Example 15
Preparation of tris(5-chloro-8-hydroxyquinolinato) aluminum from 5-chloro-8-hydroxyquinoline and Aluminum Stearate in Toluene.

A 1.5 g sample of 5-chloro-8-hydroxyquinoline was dissolved in 75 mL of hot toluene in a 125 mL Erlenmeyer flask. Aluminum stearate (2.0 g) was added and a yellow color developed almost immediately. The reaction was stirred at reflux for 18 hours during which time a yellow precipitate formed. The reaction was cooled to room temperature and the precipitate was collected by filtration and was washed with toluene and petroleum ether. After air drying, 1.17 g of tris(5-chloro-8-hydroxyquinolinato) aluminum was obtained as a yellow solid.

Other embodiments of the invention are within the scope of the following claims.

What is claimed is:

1. A method of making metal (8-quinolinolato) complexes comprising combining a metal carboxylate material in an appropriate organic solvent with an 8-hydroxyquinoline compound represented by the following Formula I

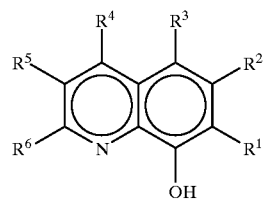

where $R^6$=hydrogen and $R^1$–$R^5$=hydrogen, halogen, ayano, alkyl, aryl, alkoxy, aryloxy, part of a fused aromatic or aliphatic ring system, and each $R^1$–$R^5$ group may incorporate further substituents and wherein said metal (8-quinolinolates) compounds are represented by the following Formula II:

$$M(L)_x$$

where M is a metal, L is a liaiand formed from the Formula I compound, and x is 2 or 3.

2. The method of claim 1 wherein the metal carboxylate material is combined with three equivalents of the 8-hydroxyquinoline compound to produce a metal tris(8-quinolinolate).

3. The method of claim 1 wherein one or more reaction byproducts are also at least partially soluble in the organic solvent.

4. The method of claim 1 wherein the metal carboxylate is combined with at least two different 8-hydroxyquinoline compounds to produce a mixed ligand metal (8-quinolinolate).

5. The method of claim 1 wherein the metal (8-quinolinolate) reaction product is an aluminum tris(8-quinolinolate).

6. The method of claim 1 wherein the metal (8-quinolinolate) reaction product is a zinc bis(8-quinolinolate).

7. The method of claim 1 wherein at least one reactant, and optionally at least one byproduct, is soluble in water.

8. The method of claim 1 wherein the carboxylate is selected from the group consisting of aluminum stearate, aluminum lactate, and zinc acetate.

9. The method of claim 1 wherein the carboxylate is aluminum lactate and the solvent is ethanol.

10. The method of claim 1 wherein the carboxylate is aluminum stearate and the solvent is toluene.

11. The method of claim 1 wherein the carboxylate is zinc acetate and the solvent is methanol.

12. The method of claim 1 further comprising purifyinig the resulting metal (8-quinolinolate) by a method selected from the group consisting of recrystallization, sublimation, and Soxhlet extraction.

13. The method of claim 1 wherein the ligand is selected from the group consisting of 5-(diphenylamino)-8-quinolinol, 7,8,9,10-tetrahydro-6-methyl-4-phenanthridinol, 3,5,7-trichloro-8-quinolinol, 3-decyl-8-quinolinol, 5-[(nonyloxy)methyl]-8-quinolinol, 3-allyl-8-hydroxyquinoline, 4-phenanthridinol, benzo[f]quinolin-5-ol, 5-chloro-8-hydroxyquinoline, 5,7-dichloro-8-hydroxyquinoline, 5-methyl-8-hydroxyquinoline, and 4-methyl-8-hydroxyquinoline.

* * * * *

UNITED STATES PATENT AND TRADEMARK OFFICE
CERTIFICATE OF CORRECTION

PATENT NO. : 6,362,339 B1
DATED : March 26, 2002
INVENTOR(S) : McCormick, Fred B.

It is certified that error appears in the above-identified patent and that said Letters Patent is hereby corrected as shown below:

Title page,
Item [56], References Cited, OTHER PUBLICATIONS, "Hiratani, Chemical Abstracts 125:167808, 1995." should read -- Hiratani, Chemical Abstracts 125:167808, 1996. --.

Column 2,
Line 39, "derivative" should read -- derivatives --.

Column 3,
Line 57, "yields This" should read -- yields. This --.

Column 5,
Line 48, "8-hydroxyguinoline" should read -- 8-hydroxyquinoline --.

Column 6,
Line 4, "filtrate. the" should read -- filtrate. The --.
Line 53, "200 ÅN,N'-bis(3-" should read -- 200Å N,N'-bis(3- --.
Line 54, "350 ÅA1Q," should read -- 350Å A1Q, --.
Line 55, "10 ÅliF," should read -- 10Å LiF, --.

Column 7,
Line 22, "(phenolate) aluminum from Pluminum" should read -- (phenolato) aluminum from Aluminum --.
Line 23, "hydroxyQuinoline," should read -- hydroxyquinoline --.
Line 38, "(phenolate) should read -- (phenolato) --.
Line 64, "(phenolate) should read -- (phenolato) --.

Column 8,
Line 12, "(phenolate) should read -- (phenolato) --.
Line 14, "hydroxyguinoline," should read -- hydroxyquinoline --.
Line 27, "(phenolate) should read -- (phenolato) --.
Line 55, "hydroxyciquinolinato" should read -- hydroxyquinolinato --.

UNITED STATES PATENT AND TRADEMARK OFFICE
CERTIFICATE OF CORRECTION

PATENT NO. : 6,362,339 B1
DATED : March 26, 2002
INVENTOR(S) : McCormick, Fred B.

It is certified that error appears in the above-identified patent and that said Letters Patent is hereby corrected as shown below:

<u>Column 9,</u>
Line 21, "hydroxvguinolinato)" should read -- hydroxyquinolinato --.
Line 22, "hydroxyguinoline" should read -- hydroxyquinoline --.

<u>Column 10,</u>
Line 29, "ayano," should read -- cyano, --.
Line 66, "purifyinig" should read -- purifying --.

Signed and Sealed this

Twenty-fourth Day of December, 2002

JAMES E. ROGAN
*Director of the United States Patent and Trademark Office*